US012635988B2

(12) United States Patent
Amadou et al.

(10) Patent No.: US 12,635,988 B2
(45) Date of Patent: May 26, 2026

(54) AUGMENTING ULTRASOUND SIMULATIONS USING CT DATA

(71) Applicant: Siemens Healthineers AG, Forchheim (DE)

(72) Inventors: Abdoul Aziz Amadou, London (GB); Paul Klein, Princeton, NJ (US)

(73) Assignee: Siemens Healthineers AG, Forchheim (DE)

( * ) Notice: Subject to any disclaimer, the term of this patent is extended or adjusted under 35 U.S.C. 154(b) by 172 days.

(21) Appl. No.: 18/345,245

(22) Filed: Jun. 30, 2023

(65) Prior Publication Data

US 2025/0000492 A1    Jan. 2, 2025

(51) Int. Cl.
    *A61B 8/00*        (2006.01)
    *G06T 7/00*        (2017.01)

(52) U.S. Cl.
    CPC ............ *A61B 8/5207* (2013.01); *A61B 8/483* (2013.01); *G06T 7/00* (2013.01); *G06T 2207/20081* (2013.01)

(58) Field of Classification Search
    None
    See application file for complete search history.

(56) References Cited

U.S. PATENT DOCUMENTS

2012/0087463 A1* 4/2012 Greenberg ................ G01T 1/29
                                                    378/207

2019/0021677 A1* 1/2019 Grbic ......................... G06T 7/11
2019/0172188 A1* 6/2019 Schmidt ................ A61B 6/032
2024/0237956 A1* 7/2024 Gong ..................... A61B 6/032

OTHER PUBLICATIONS

Vitale et al., "Improving realism in patient-specific abdominal ultrasound simulation using CycleGANs," (Aug. 7, 2019), International Journal of Computer Assisted Radiology and Surgery (2020) 15:183-192. (Year: 2019).*
Cambet et al., "High performance ultrasound simulation using Monte-Carlo simulation: a GPU ray-tracing implementation," (Nov. 3, 2020), 16th International Symposium on Medical Information Processing and Analysis, Proc. of SPIE vol. SIP220, SIP22000. (Year: 2020).*
Nasser et al., "Simulating Ultrasound images from CT Scans," (Jan. 18, 2023), medRxiv 2023.01.16.23284615. (Year: 2023).*
Kutter, Oliver, Ramtin Shams, and Nassir Navab. "Visualization and GPU-accelerated simulation of medical ultrasound from CT images." Computer methods and programs in biomedicine 94.3 (2009): 250-266.
Shams, Ramtin, Richard Hartley, and Nassir Navab. "Real-time simulation of medical ultrasound from CT images." Medical Image Computing and Computer-Assisted Intervention-MICCAI 2008: 11th International Conference, New York, NY, USA, Sep. 6-10, 2008, Proceedings, Part II 11. Springer Berlin Heidelberg, 2008.

(Continued)

*Primary Examiner* — Keith M Raymond
*Assistant Examiner* — Ashish S. Jasani

(57) ABSTRACT

Systems and methods augmenting ultrasound simulations using photon counting computed tomography (CT) data in order to create simulated ultrasound data with fine tissue detail. A virtual volume is generated from acoustic properties derived from the photon counting CT data. Simulated ultrasound data is generated by placing a simulated transducer at various positions in the virtual volume.

16 Claims, 6 Drawing Sheets

(56) References Cited

OTHER PUBLICATIONS

Tomar, Devavrat, et al. "Content-preserving unpaired translation from simulated to realistic ultrasound images." Medical Image Computing and Computer Assisted Intervention-MICCAI 2021: 24th International Conference, Strasbourg, France, Sep. 27-Oct. 1, 2021, Proceedings, Part VIII 24. Springer International Publishing, 2021.

Wein, Wolfgang, et al. "Simulation and fully automatic multimodal registration of medical ultrasound." Medical Image Computing and Computer-Assisted Intervention-MICCAI 2007: 10th International Conference, Brisbane, Australia, Oct. 29-Nov. 2, 2007, Proceedings, Part I 10. Springer Berlin Heidelberg, 2007.

Willemink, Martin J., et al. "Photon-counting CT: technical principles and clinical prospects." Radiology 289.2 (2018): 293-312.

Amadou, A. A., et al. "An Automated Pipeline for Large-Scale and Patient-Specific Ultrasound Simulation", IEEE Transactions on Medical Imaging; 2022.

* cited by examiner

AUGMENTING ULTRASOUND SIMULATIONS USING CT DATA

FIELD

This disclosure relates to generating simulated data such as used in medical imaging.

BACKGROUND

Ultrasound is an imaging modality that is often used for diagnostic and/or interventional purposes due to its low-cost, accessibility and the lack of ionizing radiation. Ultrasound allows clinicians to assess organs' functionality and structure in real-time, which can provide useful information in diagnostic settings, and complement other imaging modalities in interventional ones. However, ultrasound scans vary in quality due to operator skill and their interpretation and annotation requires extensive knowledge due to the imaging artefacts and the inherent noisy property of the modality. Automating the acquisition and analysis of ultrasound scans may improve medical image analysis and patient outcomes.

Simulated ultrasound data may be used for training automated image analysis and classification that are supported by deep learning algorithms. Deep learning methods have been shown to provide superior performance but need a high-quality training dataset with a large number of samples. The availability of such datasets is rare due to data privacy or the lack of data sharing practices among institutes. In addition, interventional datasets are harder to acquire as they are not routinely saved, crippling the development of automated image analysis tools to support specific procedures. In another application, using simulated data to train operators may allow for faster and more efficient use of ultrasound scans.

However, the usefulness of the synthetic/simulated data may be limited when training an operator or a deep learning process. Data may be simulated using generative neural networks or using physics-based methods. Data simulated with neural networks has a high degree of realism but has limited capacity in representing anatomical details with fidelity. Indeed, there are no explicit geometrical constraints applied when generating simulations with neural networks. Moreover, there are no neural network-based methods capable of using input data from another modality and to produce a faithful ultrasound simulation from it. Data generated from physics-based methods will have accurate geometry but may lack accurate representation of certain structures and tissues. This causes the simulated ultrasound data to look homogenous and lack fine tissue detail. Moreover, this prevents the simulation of lesions and/or artifacts as the original values from the input modality may not be used.

SUMMARY

By way of introduction, the preferred embodiments described below include methods, systems, instructions, and computer readable media for augmenting ultrasound simulations using computed tomography (CT) data in order to create simulated ultrasound data with fine tissue detail. Photon counting CT data is acquired. A simulated volume is generated from a segmentation and acoustic properties derived from the photon counting CT data. Simulated ultrasound data is generated from the simulated volume by placing a simulated transducer at various positions.

In a first aspect, a method for generating simulated ultrasound data is provided. The method includes acquiring photon counting CT data; generating a three-dimensional volume from the photon counting CT data, the three-dimensional volume comprising a plurality of voxels; deriving tissue properties for each of the voxels of the plurality of voxels from the photon counting CT data; determining acoustic properties of each of the voxels from the tissue properties; and generating the simulated ultrasound data using the three-dimensional volume and the determined acoustic properties. The method may include training a machine learned model using the generated simulated ultrasound data.

The three-dimensional volume may be generated by segmenting the photon counting CT data into a plurality of different tissues. The tissue properties may comprise a concentration of materials for each voxel of the plurality of voxels. Deriving the tissue properties includes measuring energy deposited by individual photons in the photon counting CT data; perform material decomposition based the energy deposited; and determining based on the material decomposition, the concentration of materials for each voxel of the plurality of voxels. The materials comprise at least water and calcium.

In an embodiment, determining the acoustic properties comprises determining a density for each of the voxels of the plurality of voxels and determining an acoustic impedance equal to the density times a tissue specific acoustic velocity.

In an embodiment, generating the simulated ultrasound data comprises placing a simulated transducer at a point in the three-dimensional volume and generating an image from a field of view from the point based on the acoustic properties of the voxels in the field of view.

In a second aspect, a system for generating simulated ultrasound data is provided. The system includes a photon counting CT imaging device and a control unit. The photon counting CT imaging device is configured to acquire photon counting CT data of a region of a patient. The control unit includes at least one processor and a memory and is configured to: generate a three-dimensional volume from the photon counting CT data, the three-dimensional volume comprising a plurality of voxels; compute tissue properties for each of the voxels of the plurality of voxels from the photon counting CT data; determine acoustic properties of each of the voxels from the tissue properties; and generate the simulated ultrasound data using the three-dimensional volume and the determined acoustic properties. The system may include a display configured to display the simulated ultrasound data. The system may further include a machine learned model stored in the memory, wherein the at least one processor is configured to train the machine learned model using at least the simulated ultrasound data.

In a third aspect, an apparatus is provided that includes a processor and a non-transitory memory. The non-transitory memory stores a set of machine-readable instructions which when executed by the processor cause the processor to: generate a three-dimensional volume from photon counting CT data of a patient, the three-dimensional volume comprising a plurality of voxels; derive tissue properties for each of the voxels of the plurality of voxels from the photon counting CT data; determine acoustic properties of each of the voxels from the tissue properties; and generate simulated ultrasound data using the three-dimensional volume and the determined acoustic properties.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

DETAILED DESCRIPTION

Figure 1:
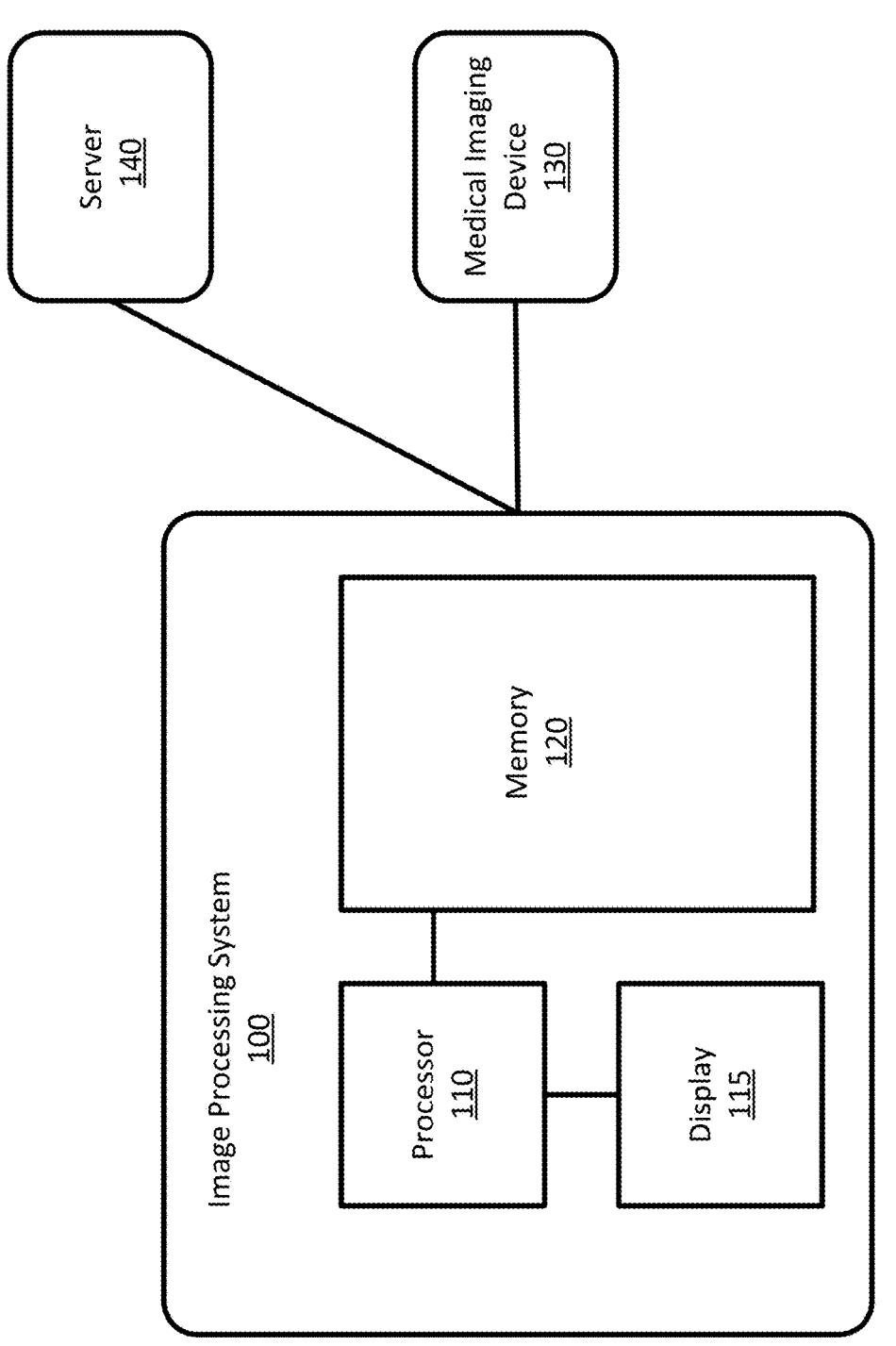
FIG. 1 depicts an embodiment of a system for augmenting ultrasound simulations using CT data.

Embodiments described herein provide systems and methods for generating simulated ultrasound data from computed tomography (CT) data, in particular photon counting CT data. A three-dimensional volume is generated from the photon counting CT data, the three-dimensional volume comprising a plurality of voxels. Tissue properties are determined for each of the voxels of the plurality of voxels from the photon counting CT data. Acoustic properties of each of the voxels are determined from the tissue properties. Simulated ultrasound data is generated using the three-dimensional volume and the acoustic properties of each of the voxels.

Diagnostic ultrasound, also called sonography or diagnostic medical sonography, is an imaging method that uses sound waves to produce images of structures within an object or patient, for example based on the acoustic properties of the materials/tissues that are being imaged. The images may provide valuable information for diagnosing and directing treatment for a variety of diseases and conditions. Most ultrasound examinations are done using an ultrasound device outside the patient, though some involve placing a small device inside the patient.

Ultrasound has certain advantages but also unique challenges that include low imaging quality and high variability. One way to deal with these challenges and others is to use automated image analysis. Advanced automatic image analysis methods may assist in diagnosis and/or to make such assessment more objective and accurate. Deep learning has recently emerged as the leading machine learning tool in various research fields, and especially in general imaging analysis and computer vision. Deep learning also shows huge potential for various automatic ultrasound image analysis tasks. Automating the ultrasound image acquisition task and analysis may improve acquisition reproducibility and quality of diagnosis but training such an algorithm requires large amounts of navigation data, which is typically not saved in routine examinations. Ultrasound simulation is one potential solution to this problem. Using a simulation environment and simulated data to train such a system would have several benefits. The trained model may be exposed to a varying range of anatomies and image qualities, hence improving its robustness, and the training could be done safely, preventing the wear of mechanical components and potential injuries. However, existing simulation pipelines are computationally expensive, lack the quality and features required, or do not offer streamlined pipelines to generate large patient datasets for training autonomous systems.

Different methods have been attempted to simulate the ultrasound process by solving the wave equation using various strategies. While providing accurate data, these methods take a substantial amount of time to generate images (in the order of several minutes to hours), which is not scalable for large-scale training. Another approach has been to perform the simulation by modelling the sound wave as a ray. These methods are based on ray casting and directly used Hounsfield Unit (HU) values to model attenuation and reflections of the ultrasound wave. However, simulation quality is limited as these methods do not account for multiple reflections and directly used HU values to compute reflections and attenuation.

Other methods generate synthetic ultrasound images by directly sampling scatterers' intensities from template ultrasound images and using electromechanical models to apply cardiac motion. These methods require pre-existing ultrasound recordings for a given patient and do not allow for simulating different type of organs other than, for example, the heart. Generative adversarial networks (GANs) have also been used for image synthesis. GANs have been used for generating images directly from segmentations, calibrated coordinates, or for improving the quality of images generated from CRT simulators. However, using GANs comes with several challenges. For example, GANs require specifically tailored training data or may suffer mode collapse when generating images for poses where training data was not available. GANs may also distort an anatomy of the patient or introduce unrealistic image artefacts. GAN enhanced synthetic data and segmentation-based simulations may also lack accurate representation of any structure that is not depicted in the masks. In such, pathologies and anatomical variations may both be omitted from the simulated images.

In another method that serves as the basis for the following disclosure a simulation pipeline has been proposed that uses segmentations from other modalities, an optimized volumetric data representation and GPU-accelerated Monte Carlo path tracing to generate ultrasound images. Advantages of this method includes an automatic pre-processing pipeline that enables the processing of thousands of patient datasets and modelling of arbitrary scenes, the reproduction of several imaging artefacts and image generation in less than a second. This method, however, may also lack the level of fine tissue detail that is required.

Each of these proposed methods for simulating ultrasound data have drawbacks that prevent the methods from achieving their goal of efficient, quick, and accurate simulated data. Embodiments described herein provide systems and methods for efficiently generating synthetic ultrasound data with fine tissue detail. This is enabled by the use of photon-counting CT material maps that provide spatial distributions of given materials. The use of photon-counting CT data for the simulation provides for the ability to generate ultrasounds with high-fidelity with regards to the anatomical content of a dataset. Lesions and tissue homogeneities are represented accurately which enables both the training of operators and a wide range of deep learning algorithms on such data. An additional advantage is in the representation of varying tissue texture and density. The increased and more accurate variations in the training data may increase the robustness of any machine learning based algorithm trained on such data, while enabling other applications such as disease detection.

FIG. 1 depicts an example system for augmenting ultrasound simulations using CT data. The system includes an image processing system 100, a medical imaging device 130, and optionally a server 140. The server 140 may be configured to perform any of the tasks of the image processing system 100 including processing and/or storing of the data and models. The server 140 may be or include a cloud-based platform. The image processing system 100 includes a processor 110, a memory 120, and a display 115. The image processing system 100 may be included with or coupled to the medical imaging device 130. The image processing system 100 is configured to generate simulated/synthetic ultrasound data from photon counting CT data generated by the medical imaging device or other medical imaging system. In an embodiment, the photon counting CT data may be previously acquired and stored in the memory 120 or at the server 140. Certain imaging functions may be performed by any of the image processing system 100, the medical imaging device 130, or the server. The image processing system 100 may also be configured to train or store a machine learned model using the simulated ultrasound data. Imaging data may be acquired from the medical imaging device 130 in real time or may be generated, stored, and processed at a later time.

Figure 2:
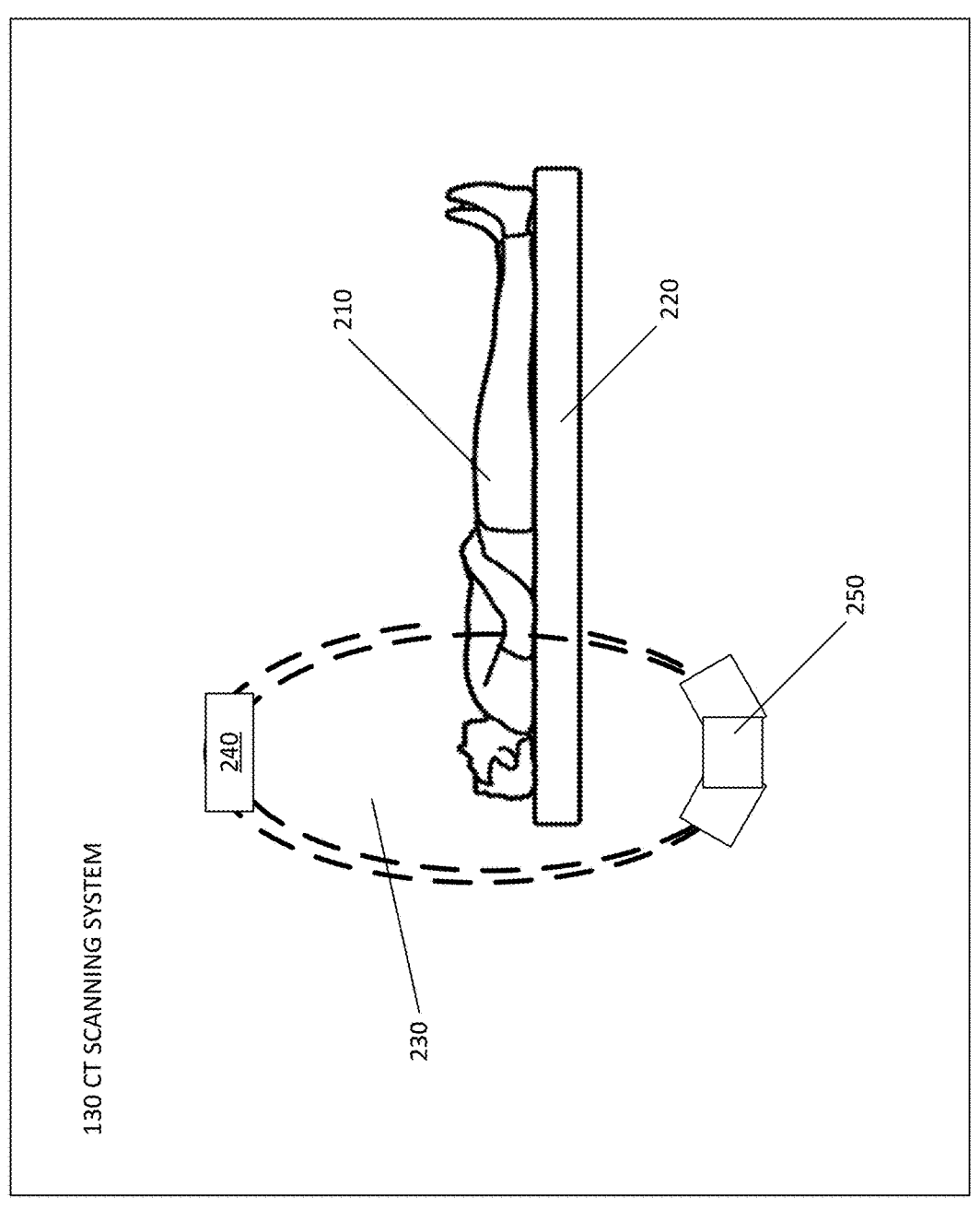
FIG. 2 depicts an example CT imaging system.

FIG. 2 depicts an example photon counting CT imaging system 130 that is configured to acquire photon counting CT data. The photon counting CT scanner 130 is only exemplary, and a variety of CT scanning systems can be used to collect the photon counting CT data with different configurations. In an embodiment, other imaging systems that collect information for material composition maps may be used. In the photon counting CT imaging system 130 of FIG. 2, an object 210 (e.g., a patient 210) is positioned on a table 220 that is configured, via a motorized system, to move the table 220 to multiple positions through a circular opening 230 in the photon counting CT scanner 130. An X-ray source 240 (or other radiation source) and detector element(s) 250 are a part of the photon counting CT scanner 130 and are configured to rotate around the subject 210 on a gantry while the subject is inside the opening/bore 230. The rotation may be combined with movement of the bed to scan along a longitudinal extent of the patient 210. Alternatively, the gantry moves the source 240 and detector 250 in a helical path about the patient 210. In a photon counting CT scanner 130, a single rotation may take approximately one second or less. During the rotation of the X-ray source 240 and/or detector, the X-ray source 240 produces a narrow, fan-shaped (or cone-shaped) beam of X-rays that pass through a targeted section of the body of the subject 210 being imaged. The detector element(s) 250 are opposite the X-ray source 240 and register the X-rays that pass through the body of the subject being imaged and, in that process, record a snapshot used to create an image. Many different snapshots at many angles through the subject are collected through one or more rotations of the X-ray source 240 and/or detector element(s) 250. The image data generated by the collected snapshots are transmitted to the image processing system 100 that stores or processes the image data based on the snapshots into one or several cross-sectional images or volumes of an interior of the body (e.g., internal organs or tissues) of the subject being scanned by the photon counting CT scanner 130. Any now known or later developed photon counting CT scanner may be used. Other x-ray scanners, such as a CT-like C-arm scanner, may be used.

Conventional medical CT systems are equipped with solid-state scintillation detector elements (such as energy-integrating detectors (EIDs). In a two-step conversion process, the absorbed X-rays are first converted into visible light in the scintillation crystal. The light is then converted into an electrical signal by a photodiode attached to the backside of each detector cell. Photon Counting CT is a type of CT imaging that utilizes a direct conversion X-ray detector where incident X-ray photon energies are directly recorded as electronical signals. Photon Counting Detectors (PCDs) directly convert deposited X-ray energy to an electronic signal, as a large voltage is applied across the semiconductor, creating electron hole pairs when a photon hits the detector. By using energy-resolving detectors instead of EIDs, photon-counting CT systems are able to count individual incoming x-ray photons and measure their energy. The energy information may then be used for generating an image and other tasks such as material decomposition. For material decomposition, energy-selective images are generated from the number of registered counts in each energy bin. From these images, a set of material concentration maps is generated through a data-processing method known as material decomposition. Material concentration maps may be used in generating an image but also assisting in augmenting the simulated ultrasound data with fine tissue data.

The medical imaging device 130 is configured to generate simulated ultrasound data using the photon-counting CT. The photo-counting CT information may be used to determine acoustic properties which are used to generate the simulated data. Using photon-counting CT, the concentration of given materials per voxel (mmol/L) is determined. The molar mass for each material is a known value from the literature (g/mol). This provides the mass of the substance per liter (g/L), which in turn can be turned into density ρ. An acoustic impedance of the substance may be calculated as $Z=\rho V$ wherein V is the tissue specific acoustic velocity.

The simulated ultrasound data is data representing a two-dimensional slice or a three-dimensional volume of the simulated subject. In an embodiment, a three-dimensional scene/virtual environment is created from the photon-counting CT data. A simulated transducer is placed at any point in the scene to provide an orientation. Simulated ultrasound data is generated from the perspective of the simulated transducer. The simulated data may be in any format. While the terms image and imaging are used, the image or imaging data may be in a format prior to actual display of the image. For example, the simulated image may be black and white or a plurality of red, green, blue (e.g., RGB) values output to a display 115 for generating the image in the display format.

Figure 3:
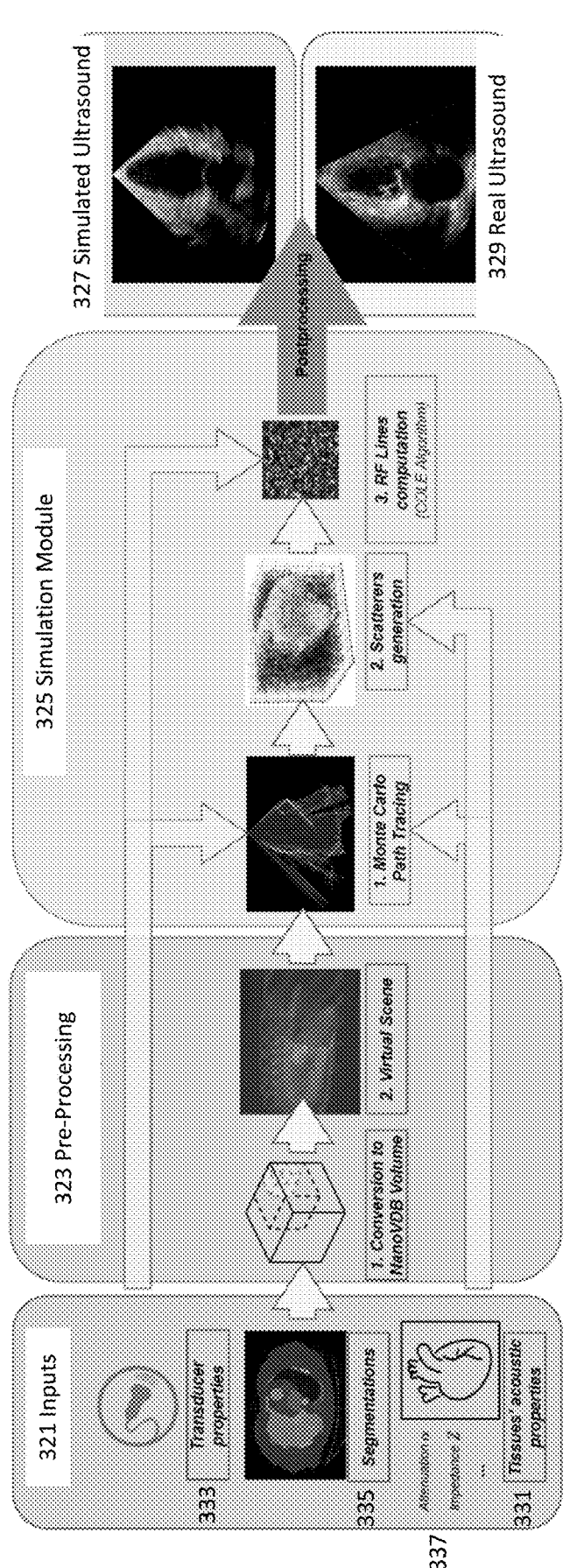
FIG. 3 depicts a simulation pipeline according to an embodiment.

FIG. 3 depicts an example of the simulation pipeline. The simulated pipeline has three main stages 321 inputs, 323 preprocessing, and 325 simulation module. The simulated pipeline is configured to generate a simulated ultrasound image 327. The simulation pipeline takes as input segmentations 335 of the CT data, attenuation values, impedance values 337, transducer properties 333, and acoustic properties 331. The inputs are used to create a virtual scene. Simulated data is then generated using different image generation methods. As described in FIG. 3, in an embodiment, using input segmentations 335 from other modalities, transducer and tissue acoustic properties the system 100 converts the segmentation to a NanoVDB volume for raytracing on a GPU. The sound waves may be modeled as rays. The system 100 performs raytracing to simulate their propagation. A scattering volume is generated, and the RF lines are computed. Envelope detection, time-gain compensation, dynamic range adjustment and scan conversion are performed to yield the final simulation. In FIG. 3, a real ultrasound 329 is shown for qualitative comparison next to the simulated ultrasound image. The simulation pipeline is quick, efficient, and provides accurate simulated data that includes fine tissue data including representations of lesions and other abnormalities.

The input data to the simulation pipeline includes the photon counting CT data and information derived therefrom, for example a segmentation 335 and the acoustic properties 331. The photon counting CT data may represent a two or three-dimensional region of the subject. For example, the photon counting CT data represents an area or slice of the subject as pixel values or voxel values. As another example, the photon counting CT data represents a volume or three-dimensional distribution of voxels. The three-dimensional representation may be formatted as a stack or plurality of two-dimensional planes or slices. Values are provided for each of multiple locations distributed in two or three dimensions. The CT imaging data is acquired as one or more frames of data. The frame of data represents the scan region at a given time or period. The dataset may represent the area or volume over time, such as providing a 4D representation of the subject.

The photon counting CT data is processed by the image processing system 100. The image processing system 100 includes a processor 110, display 115, and memory 120. The image processing system 100 may receive or transmit data to and from the server 140 that may also be configured to process the image or store data for future image processing or training/storage of machine trained models. The image processing system 100 inputs the photon counting CT data and outputs a segmented image or volume that is used as input to the simulation pipeline. The image processing system 100 is further configured to calculate the acoustic properties 331 of the voxels from the photon counting CT data. The additional inputs may be determined by the image processing system 100 or provided by a user or other datastore/processing system.

The processor 110 is a general processor, digital signal processor, graphics processing unit, application specific integrated circuit, field programmable gate array, artificial intelligence processor, digital circuit, analog circuit, combinations thereof, or other now known or later developed device for processing the photon counting CT data and generating simulated ultrasound data, among other processes described below. The processor 110 is a single device, a plurality of devices, or a network. For more than one device, parallel or sequential division of processing may be used. Different devices making up the processor 110 may perform different functions. In one embodiment, the processor 110 is a control processor or other processor of the medical imaging device 130. In other embodiments, the processor 110 is part of a separate workstation or computer. The processor 110 operates pursuant to stored instructions to perform various acts described herein. The processor 110 is configured by software, design, firmware, and/or hardware to perform any or all of the acts of FIG. 4 and any other computations described herein.

In an embodiment, the processor 110 is configured to perform segmentation, for example using a machine trained model. The processor 110 is configured to segment the photon counting CT data provided by the medical imaging device 130 to generate a segmented image or volume. Image segmentation extracts or identifies regions of interest (ROI) through a semiautomatic or automatic process. Segmentation divides an image into areas based on a specified description, such as segmenting body organs/tissue (skin, bone, muscle, internal organs, vessels, and/or central nervous system. The segmented data may be used for different applications such as border detection, tumor detection/segmentation, and mass detection. Here, the segmented data is used to create the simulated environment from which the simulated ultrasound data is generated. In the segmented volume, the tissues and organs are outlined in the underlying photon counting CT data and, for example, provided with different colors or shades of grey to distinguish between types. The segmentation may be provided by a segmentation model and the output of the medical imaging device 130. Different types of models or networks may be trained and used for the segmentation task. The segmented data includes a plurality of voxels. Each voxel represents a three-dimensional display element. For example, a voxel represents a quantity of 3D data just as a pixel is a point or cluster of points in two-dimensional data. Each voxel of the segmented data may be provided with acoustic properties 331.

The acoustic properties 331 are computed or derived from the photon counting CT data. Using photon-counting CT, the concentration of given materials per voxel (mmol/L) is computed. With known molar masses from the literature (g/mol), the mass of the substance per liter (g/L) may be computed which in turn may be turned into density ρ. The acoustic impedance of each voxel is calculated using Z=ρV where V is the tissue specific acoustic velocity.

The concentration of given materials is determined using a material decomposition process. During the acquisition of the photon counting CT data, the energy deposited by individual photons is measured. Material decomposition is performed using this energy information. Material decomposition gives the concentration of given materials for each voxel. This allows for the creation of material maps, giving the distribution of a given material in the image. The material maps are used with other data acquired though CT scanning in order to determine the acoustic properties 331. For CT scanning, CT HU Values are linked to the tissue density at a given position. Namely:

$$HU = 1000 \frac{\mu - \mu_{water}}{\mu_{water} - \mu_{air}}$$

where $\mu_{water}$ and $\mu_{air}$ are the linear attenuation coefficients for water and air. The HU values depend on several acquisition parameters including the Tube Voltage (or KvP), filters that change the photon distribution and thus the energy spectra, and the reconstruction kernel. The tube voltage (KvP) limits the maximum photon energy (keV) emitted. Given a keV value, the system 100 can retrieve the mass attenuation coefficient per tissue (measured and available in the literature). The mass attenuation coefficient is defined as $$\sigma = \frac{\mu}{\rho}$$

with ρ being the tissue density. Finally, given a density from the material decomposition, the system 100 can calculate the acoustic impedance at a given point/voxel with: Z=ρV with V equal to the speed of sound in the given medium, e.g., the tissue specific acoustic velocity. With the acoustic impedance, the system 100 is able to model reflections happening within the respective tissue, i.e., in an area of an organ far from boundaries. By knowing the exact tissue properties at a given voxel, it is possible to use, voxel-wise, the corresponding acoustic properties 331 during the simulation and thus reproduce the tissue inhomogeneities with great accuracy.

Figure 4:
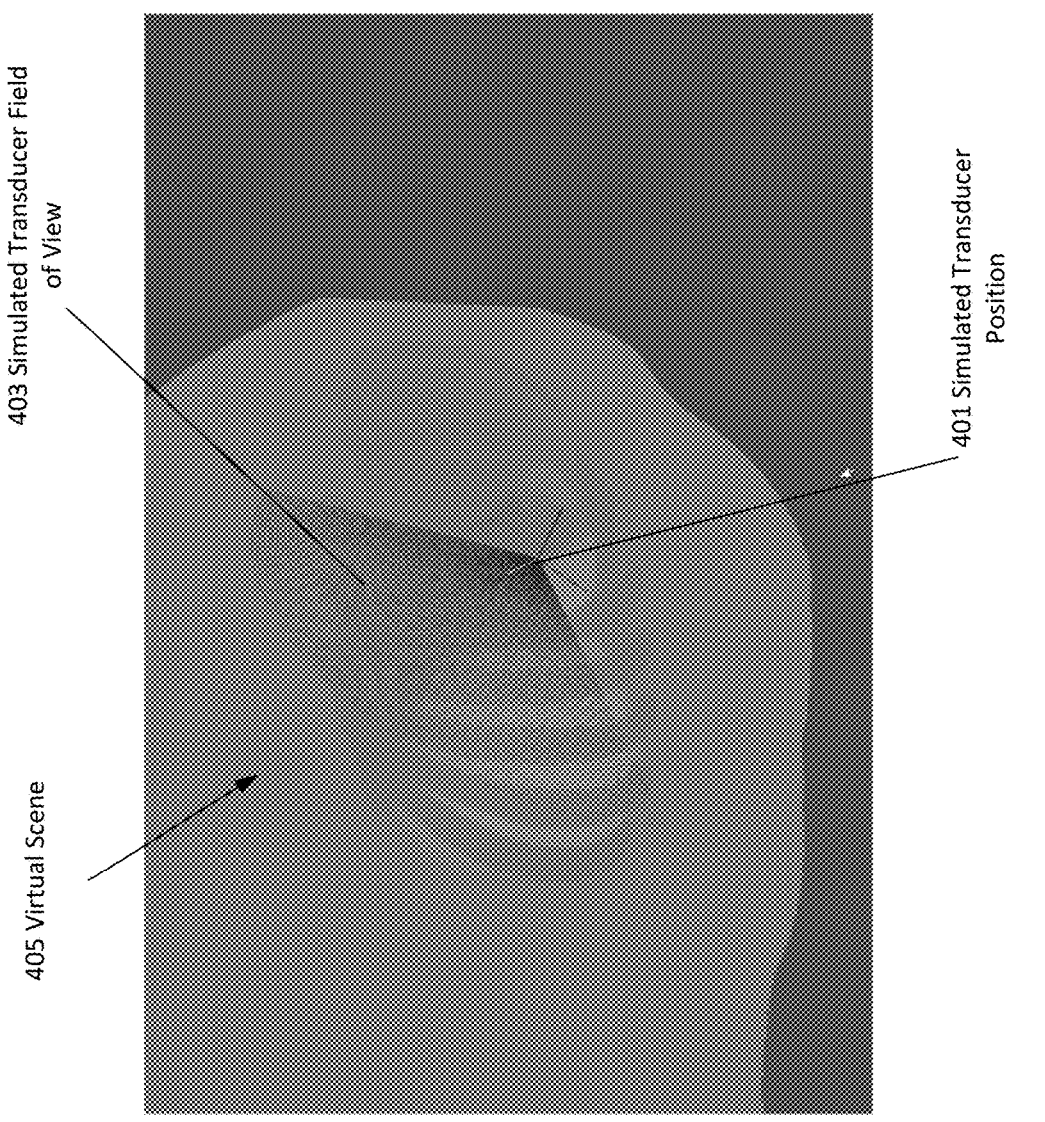
FIG. 4 depicts an example virtual scene according to an embodiment.

Continuing in the simulation pipeline of FIG. 3, the system 100 is configured to generate a virtual scene or volume of a region of a virtual patient using the segmented CT data. FIG. 4 depicts an example virtual scene 405. The virtual scene includes a simulated transducer position 401 and a simulated transducer field of view 403. Simulated ultrasound data is generated by determining the acoustic properties 331 of the voxels in the simulated field of view and simulating the actions of the transducer. In an embodiment the virtual scene 405 is generated from the segmentation volume with all labels which is converted to a NanoVDB grid. The grid is used during ray tracing to access a label associated with a given voxel. Then, for each label in the segmentation volume, a narrowband signed distance function (SDF) is computed such that the distance from voxels in the neighborhood of the organ to its boundary is known. The SDF grids are written to the output volume and are later used during traversal to compute smooth surface normals by looking at the SDF's gradient. A separate grid containing only the voxels associated with the current organ is also saved in the output volume. Hence, the final NanoVDB volume contains the original voxel grid and, for each label, two grids: the SDF grid as well as the voxel grid. The preprocessing may take less than five minutes per volume. Several worker processes may be used to perform this task on multiple volumes in parallel.

The goal of the simulation module of FIG. 3 is to generate view-dependent ultrasound images. This module performs the ray tracing using OptiX and models large-scale effects (reflections, refractions, and attenuation). This is done by computing, for each point along a scanline, the intensity I sent back to the transducer. A second part generates the ultrasound image by convolving the point spread function (PSF) with the scatterer distribution while taking into account the corresponding intensity I(1) along the scanline.

The output of the simulation pipeline is a synthetic ultrasound image (d) that includes fine tissue detail due to the use of the acoustic properties 331 derived from the photon counting CT data. An example of a real ultrasound is also shown in FIG. 3 for comparison. Multiple images or sets of images may be generated using the simulated scene using the simulation pipeline by moving the transducer to different locations and generating a new image. The simulations may be used for different purposes. In an example, operators may be trained using the simulated environment. In another example, the simulated ultrasound data may be used to train a model/neural network using the simulated ultrasound data.

The model may be configured to perform automated acquisition or analysis of the ultrasound data. For training the model, the simulated ultrasound data may be acquired at any point prior to inputting the training data into the model. For supervised training, annotations may be provided with the simulated ultrasound data. The training of the model includes acquiring the simulated ultrasound data and inputting the simulated ultrasound data into the model over and over again while adjusting the parameters/weights of the model based on a comparison between the output of the model and the input training data/annotations. One trained, the model may be applied for its purpose, for example, automated acquisition or analysis of ultrasound data. The training may be performed at any point prior to the application of the model. The training may be repeated after new simulated ultrasound data is acquired. The application may be performed at any point after the training generates the trained network and real-time data is received.

In an embodiment, the machine learned network(s) or model(s) include a neural network that is defined as a plurality of sequential feature units or layers. Sequential is used to indicate the general flow of output feature values from one layer to input to a next layer. Sequential is used to indicate the general flow of output feature values from one layer to input to a next layer. The information from the next layer is fed to the next layer, and so on until the final output. The layers may only feed forward or may be bi-directional, including some feedback to a previous layer. The nodes of each layer or unit may connect with all or only a sub-set of nodes of a previous and/or subsequent layer or unit. Skip connections may be used, such as a layer outputting to the sequentially next layer as well as other layers. Rather than pre-programming the features and trying to relate the features to attributes, the deep architecture is defined to learn the features at different levels of abstraction based on the input data. The features are learned to reconstruct lower-level features (i.e., features at a more abstract or compressed level). Each node of the unit represents a feature. Different units are provided for learning different features. Various units or layers may be used, such as convolutional, pooling (e.g., max pooling), deconvolutional, fully connected, or other types of layers. Within a unit or layer, any number of nodes is provided. For example, 100 nodes are provided. Later or subsequent units may have more, fewer, or the same number of nodes.

As described above, data simulation has been a key enabler for creating machine learning algorithms where curating large training sets were challenging. However, the usefulness of the synthetic data has been limited when the algorithm must attend to specific anatomical structures which could not be well represented. For example, in the context of cardiac ultrasound, the tracking algorithms often need to rely on tracking visual features of the cardiac valves. For cardiac ultrasound, the usefulness of mask derived simulations is limited as certain features are unlikely to be well represented in the synthetic data. However, using the simulation pipeline described herein, fine tissue detail may be included and thus allow for more accurate training data and thus more comprehensive models/machine learning algorithms. An additional advantage can be found in the representation of varying tissue texture and density. Having such variations in the training could increase the robustness of any machine learning based algorithm, while enabling other applications such as disease detection. The use of photon-counting CT data for the simulation allows for the system 100 to generate ultrasounds with high-fidelity with regards to the anatomical content of a dataset. Lesions and tissue homogeneities are represented accurately, which enables the training of a wide range of AI algorithms on such data.

The simulated pipeline, simulated data, photon counting CT data, and other data may be stored in the memory 120. The memory 120 may be or include an external storage device, RAM, ROM, database, and/or a local memory (e.g., solid state drive or hard drive). The same or different non-transitory computer readable media may be used for the instructions and other data. The memory 120 may be implemented using a database management system (DBMS) and residing on a memory 120, such as a hard disk, RAM, or removable media. Alternatively, the memory 120 is internal to the processor 110 (e.g., cache).

The instructions for implementing the processes, methods, and/or techniques discussed herein are provided on non-transitory computer-readable storage media or memories, such as a cache, buffer, RAM, removable media, hard drive, or other computer readable storage media (e.g., the memory 120). The instructions are executable by the processor 110 or another processor. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the instructions set, storage media, processor 110 or processing strategy and may be performed by software, hardware, integrated circuits, firmware, micro code, and the like, operating alone or in combination. In one embodiment, the instructions are stored on a removable media device for reading by local or remote systems. In other embodiments, the instructions are stored in a remote location for transfer through a computer network. In yet other embodiments, the instructions are stored within a given computer, CPU, GPU, or system. Because some of the constituent system components and method steps depicted in the accompanying figures may be implemented in software, the actual connections between the system components (or the process steps) may differ depending upon the manner in which the present embodiments are programmed.

The display 115 is configured to display or otherwise provide the model of the user to the user. The display 115 is a CRT, LCD, projector, plasma, printer, tablet, smart phone or other now known or later developed display device for displaying the output.

Figure 5:
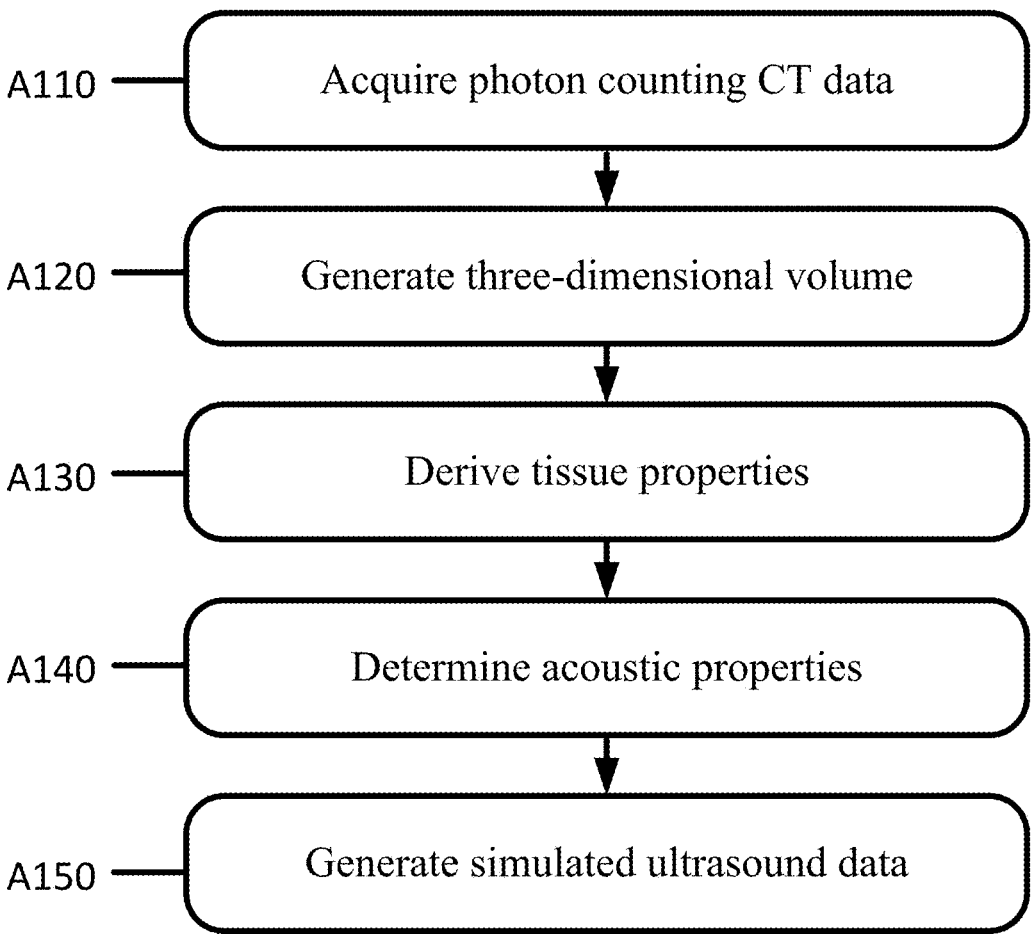
FIG. 5 depicts an example method for augmenting ultrasound simulations using CT data.

FIG. 5 depicts an example method for generating simulated ultrasound data from a CT scan. The method is performed by the system 100 of FIGS. 1, 2, the pipeline of FIG. 3 or another system. The method is performed in the order shown or other orders. Additional, different, or fewer acts may be provided.

At act A110, a system 100 acquires photon counting CT data. The photon counting CT data may be acquired at any point. In an example, the CT data is previously acquired and stored for later processing. In an example, a CT scan generates CT data which is processed in real time. The CT scan may include a plurality of image slices that when combined form a 3D volume. The photon counting CT data may be acquired using photon counting detector computed tomography. Photon counting detectors directly convert deposited X-ray energy to an electronic signal, as a large voltage is applied across the semiconductor, creating electron hole pairs when a photon hits the detector. Other CT scanners use scintillator based EIDs that emit visible light when X-rays hit them.

At act A120, the system 100 generates a three-dimensional volume from the photon counting CT data, the three-dimensional volume comprising a plurality of voxels. The system 100 may be configured to segment the CT data using a segmentation model. The CT data is input into a segmentation model that is configured to output a segmented mask when inputting CT data. Any method for segmentation may be used. For example, segmentation may be thresholding-based, region-based, shape-based, model based, neighboring based, and/or machine learning-based among other segmentation techniques. Thresholding-based methods segment the image data by creating binary partitions based on image attenuation values, as determined by the relative attenuation of structures on the images. Region-based segmentation compares one pixel in an image to neighboring pixels, and if a predefined region criterion (e.g., homogeneity) is met, then the pixel/voxel is assigned to the same class as one or more of its neighbors. Shape-based techniques use either an atlas-based approach or a model-based approach to find a lung boundary. Model-based methods use prior shape information, similar to atlas-based approaches; however, to better accommodate the shape variabilities, the model-based approaches fit either statistical shape or appearance models of the lungs to the image by using an optimization procedure. Neighboring anatomy-guided methods use the spatial context of neighboring anatomic objects of the lung (e.g., rib cage, heart, spine) for delineating lung regions. In machine learning-based methods, boundaries are predicted on the basis of the features extracted from the image data.

At act A130, the system 100 derives tissue properties for each of the voxels of the plurality of voxels from the photon counting CT data. The tissue properties may include the material composition of each of the voxels. For example, each voxel may represent a type of tissue or object that includes different materials. Liver tissue for example, may have a different material composition than a lesion or bone or other tissue/organ/vessel/structure. The material composition may be identified by using material decomposition. Material decomposition in computed tomography is a method for differentiation and quantification of materials in a sample and it utilizes the energy dependence of the linear attenuation coefficient. Material decomposition is performed by determining the full energy dependence of the attenuation curve in every image voxel. Rather than measuring the x-ray attenuation in a very large number of energy bins, a small number of energy bins is sufficient for this purpose. This is explained by the finding that any material consisting of light elements, such as human tissue, is approximately equivalent to a combination of two basis materials, as far as x-ray attenuation properties are concerned. Any pair of materials may be chosen as basis materials, for example water and calcium. Any human tissue can therefore be represented by a point in a diagram whose axes are the concentrations of the two basis materials. Although in reality human tissue is not composed of water and calcium, it has the same x-ray attenuation coefficient at all energies as the combination of these materials. Elements with high atomic numbers show a so-called k-edge, which is a step change in the attenuation at a specific x-ray energy. A k-edge in the x-ray attenuation curve identifies the corresponding element uniquely, so if a contrast agent containing a k-edge material is present, the concentration of that material is added to this diagram as a third dimension. More than two basis materials may be used to represent human tissues. For example fat may be added as an additional dimension in the diagram.

Figure 6:
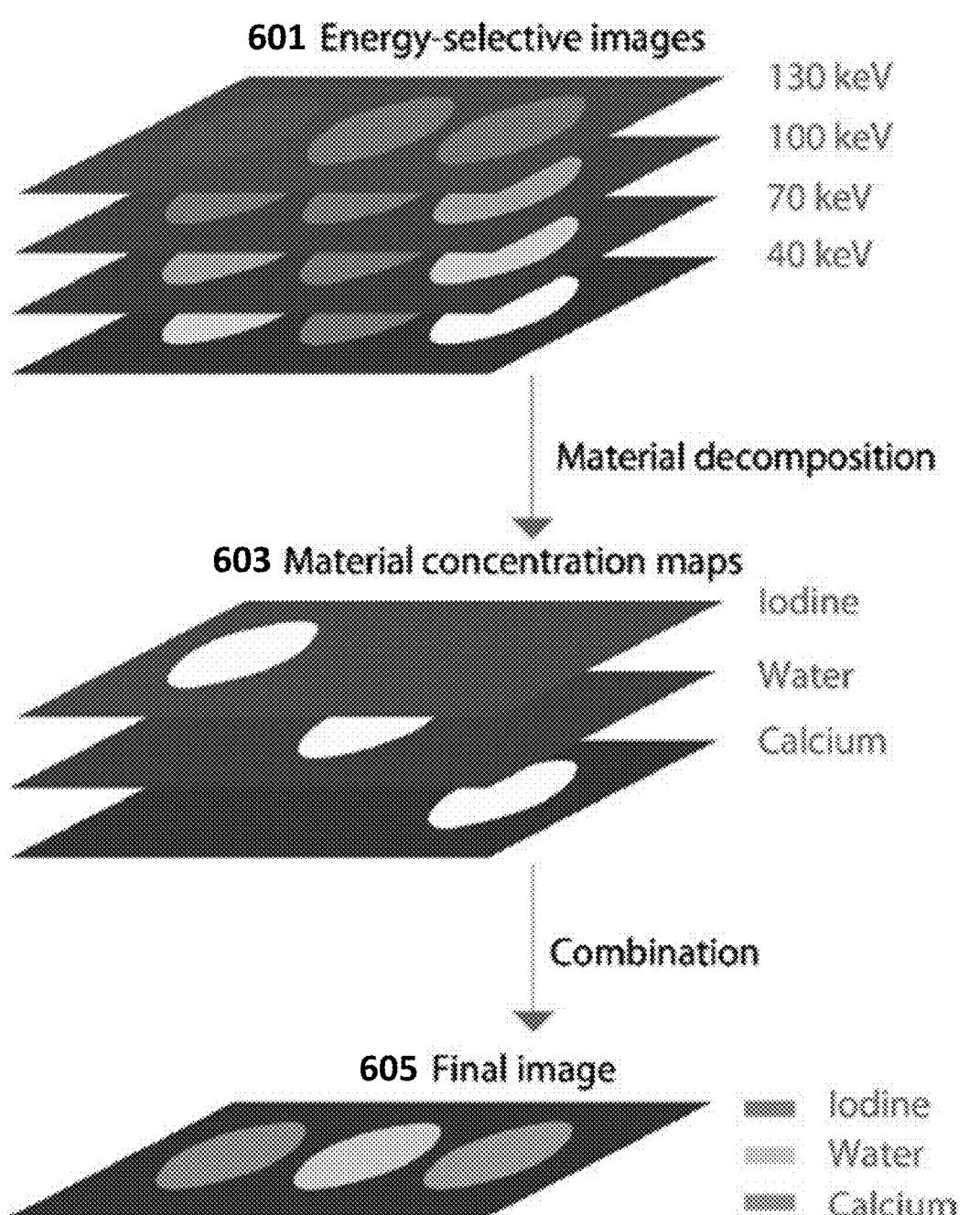
FIG. 6 depicts an example material decomposition process.

FIG. 6 depicts an example of material decomposition. Energy-selective images 601 are generated from the number of registered counts in each energy bin (here 103 key, 100 key, 70 key, and 40 kev). From these images, a set of material concentration maps 603 are generated through a data-processing method known as material decomposition. Each map 603 contains the equivalent concentration of one of the materials for each voxel in the image, here for example water, calcium, and iodine (iodine being used as a contrast in many scans). Material concentration maps 603 may be combined in different ways to form an image that is further processed below. The material concentration maps 603 are used to determine the acoustic properties 331 but may also be used to augment the segmented volume generated at act A120. In FIG. 6, the material concentration maps are used to generate an image 605. Alternative methods of material decomposition may be used such as deep learning methods. Material decomposition in dual energy CT estimates the density of two basis materials by using the linear attenuation coefficients of materials scanned at two X-ray energies as:

$$\mu(E1) = cA\mu A(E1) + cB\mu B \qquad (E1)$$

$$\mu(E2) = cA\mu A(E2) + cB\mu B \qquad (E2)$$

where $\mu_A(E_x)$ and $\mu_B(E_x)$ represent the experimentally known linear attenuation coefficients of materials A and B at energy $E_x$, and $c_A$ and $c_B$ the density of unknown basis materials A and B. The density of the materials may be estimated by finding the solution to these equations.

Current photon counting CT allows scanning in 2-8 energy bins. If the object is scanned in 2-bin mode, the method in DECT can be applied as is. If the object is scanned in 3 or more energy bins, there are additional analysis options that use further equations. Other methods such as k-edge imaging may be used.

At act A140, the system 100 determines acoustic properties 331 of each of the voxels from the tissue properties. The acoustic properties 331 may include at least acoustic impedance of the material/tissue of the voxel. Acoustic impedance is determined using the tissue density and the speed of sound in the respective tissue. The speed of sound in respective tissues may be identified from a database or other source. The density may be calculated by using CT HU Values that are linked to the tissue density at a given position. For example:

$$HU = 1000 \frac{\mu - \mu_{water}}{\mu_{water} - \mu_{air}}$$

where $\mu_{water}$ and $\mu_{air}$ are the linear attenuation coefficients for water and air. However, HU values depend on several acquisition parameters, namely—Tube Voltage (or KvP)—Filters, which change the photon distribution and thus the energy spectra—The reconstruction kernel Using HU Values in the simulation: The tube voltage (KvP) limits the maximum photon energy (keV) emitted. Given a keV value, one can retrieve the mass attenuation coefficient per tissue (measured and available in the literature). The mass attenuation coefficient is defined as $$\sigma = \frac{\mu}{\rho}$$

with $\rho$ being the tissue density. Finally, given a density, one can retrieve the acoustic impedance at a given point with: Z=$\rho$c with c the speed of sound in the given medium. With the acoustic impedance available, it is possible to model reflections happening within tissue, i.e., in an area of an organ far from boundaries.

At act A150, the system 100 generates simulated ultrasound data using the three-dimensional volume and the determined acoustic properties 331. A virtual transducer is placed at a point in a virtual scene generated from the three-dimensional volume. The acoustic properties 331 of the voxels are used to generate a simulated/synthetic ultrasound image for the field of view of the virtual transducer.

The image generation process may be repeated for different positions of the virtual transducer. Multiple volumes may be generated to provide ultrasound data over time by placing the virtual transducer in a similar position in multiple sequential volumes. The The method described above provides a simulator that generates realistic images that can be used for the generation of large number of simulated images that may be used for training supervised machine learning algorithms where the major bottleneck is the sparsity of data. This solves the challenging problem of fast simulation of realistic ultrasound images. Ultrasound images are formed by reflection of ultrasound waves off body structures. Therefore, it takes time for realistic medical ultrasound image simulation as acoustic properties 331 should be incorporated into the simulator for realistic simulation. The annotation of the simulated images is a comparatively trivial task. The simulator may also be used as a learning aid for doctors or clinicians that operate ultrasound equipment. A large variety of pathologies may be generated by the simulator, which may not be present in case limited real data is available.

It is to be understood that the elements and features recited in the appended claims may be combined in different ways to produce new claims that likewise fall within the scope of the present invention. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description. Independent of the grammatical term usage, individuals with male, female or other gender identities are included within the term.

The invention claimed is:

1. A method for generating simulated ultrasound data, the method comprising:
   acquiring photon counting CT data;
   generating a three-dimensional volume from the photon counting CT data, the three-dimensional volume comprising a plurality of voxels;
   deriving tissue properties for each of the voxels of the plurality of voxels from the photon counting CT data, wherein deriving the tissue properties comprises:
   measuring energy deposited by individual photons in the photon counting CT data;
   generating energy-selective images from a number of registered counts in each of three or more energy bins;
   generating material concentration maps based on the energy-selective images; and
   determining based on the material concentration maps, the tissue properties comprising a concentration of materials for each voxel of the plurality of voxels;
   deriving an acoustic impedance value for each of the voxels of the plurality of voxels from the photon counting CT data, wherein deriving the acoustic impedance value comprises:

determining a linear attenuation coefficient μ from the photon counting CT data at a known tube voltage;

determining a tissue density ρ from the relationship $\sigma=\mu/\rho$ using tabulated mass-attenuation coefficients σ; and computing the acoustic impedance value $Z=\rho c$ using a sound speed c associated with the voxel;

determining additional acoustic properties of each of the voxels from the tissue properties; and generating the simulated ultrasound data using the three-dimensional volume and the determined additional acoustic properties and the acoustic impedance values, wherein the simulated ultrasound data is generated at least in part by modeling reflections within tissue volumes based on spatial variations in the acoustic impedance values.

2. The method of claim 1, wherein the three-dimensional volume is generated by segmenting the photon counting CT data into a plurality of different tissues.

3. The method of claim 1, wherein the simulated ultrasound data includes one or more lesions.

4. The method of claim 1, wherein the tissue properties comprise a concentration of materials for each voxel of the plurality of voxels.

5. The method of claim 1, wherein the materials comprise at least water and calcium.

6. The method of claim 1, wherein generating the simulated ultrasound data comprises placing a simulated transducer at a point in the three-dimensional volume and generating an image from a field of view from the point based on the acoustic properties of the voxels in the field of view.

7. The method of claim 1, wherein the generated simulated ultrasound data is used as training data for a machine learned model by inputting the generated simulated ultrasound data into the machine learned model and adjusting weights of the machine learned model based on a comparison between an output of the machine learned model and the input generated simulated ultrasound data.

8. A system for generating simulated ultrasound data, the system comprising:

a photon counting CT imaging device configured to acquire photon counting CT data of a region of a patient; and a control unit comprising at least one processor and a memory, the control unit configured to:

generate a three-dimensional volume from the photon counting CT data, the three-dimensional volume comprising a plurality of voxels;

measure energy deposited by individual photons in the photon counting CT data;

generate energy-selective images from a number of registered counts in each of three or more energy bins;

generate material concentration maps based on the energy-selective images;

determine based on the material concentration maps, tissue properties comprising a concentration of materials for each voxel of the plurality of voxels;

derive, for each voxel of the plurality of voxels, an acoustic impedance value from the photon counting CT data, wherein the control unit is configured to:

determine a linear attenuation coefficient μ for the voxel from the photon counting CT data at a known tube voltage;

determine a tissue density ρ for the voxel from the relationship $\sigma=\mu/\rho$ using a tabulated mass-attenuation coefficient σ; and compute an acoustic impedance value $Z=\rho c$ for the voxel using a sound speed c associated with the voxel determine acoustic properties of each of the voxels from the tissue properties; and generate the simulated ultrasound data using the three-dimensional volume and the determined acoustic properties at least in part by modeling reflections within tissue volumes based on spatial variations in the acoustic impedance values.

9. The system of claim 8, further comprising:

a display configured to display the simulated ultrasound data.

10. The system of claim 8, further comprising:

a machine learned model stored in the memory, wherein the at least one processor is configured to train the machine learned model using at least the simulated ultrasound data by inputting the simulated ultrasound data into the machine learned model and adjusting weights of the machine learned model based on a comparison between an output of the machine learned model and the input simulated ultrasound data.

11. The system of claim 8, wherein the three-dimensional volume is generated by segmenting the photon counting CT data into a plurality of different tissues.

12. The system of claim 8, wherein generating the simulated ultrasound data comprises placing a simulated transducer at a point in the three-dimensional volume and generating an image from a field of view from the point based on the acoustic properties of the voxels in the field of view.

13. The system of claim 8, further comprising:

a deep learning model configured to perform automated image analysis or acquisition, wherein the simulated ultrasound data comprises training data for the deep learning model.

14. An apparatus comprising:

a processor; and a non-transitory memory storing therein a set of machine-readable instructions which when executed by the processor cause the processor to:

generate a three-dimensional volume from photon counting CT data of a patient, the three-dimensional volume comprising a plurality of voxels;

measure energy deposited by individual photons in the photon counting CT data;

generate energy-selective images from a number of registered counts in each energy bin;

generate material concentration maps based on the energy-selective images;

determine based on the material concentration maps, tissue properties comprising a concentration of materials for each voxel of the plurality of voxels;

determine acoustic properties of each of the voxels from the tissue properties;

determine a linear attenuation coefficient μ for each of the voxels from the photon counting CT data at a known tube voltage;

determine a tissue density ρ for each of the voxel from the relationship $\sigma=\mu/\rho$ using a tabulated mass-attenuation coefficient σ;

compute an acoustic impedance $Z=\rho c$ for each of the voxels using a sound speed c associated with the voxel; and generate simulated ultrasound data using the three-dimensional volume and the determined acoustic properties at least in part by modeling reflections within tissue volumes based on spatial variations in the determined acoustic impedance.

15. The apparatus of claim 14, wherein the photon counting CT data is acquired by a CT imaging system.

16. The apparatus of claim 14, wherein machine-readable instructions further comprise machine-readable instructions that cause the processor to:

provide the simulated ultrasound data as a training data set.

* * * * *